United States Patent
Chouinard (12)

(10) Patent No.: US 6,372,792 B1
(45) Date of Patent: *Apr. 16, 2002

(54) METHOD FOR TREATING ANXIETY, ANXIETY DISORDERS AND INSOMNIA

(76) Inventor: Guy Chouinard, 4015 Chemin Trafalgar, Montreal (CA), H3Y 1R1

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/015,850

(22) Filed: Jan. 29, 1998

Related U.S. Application Data

(63) Continuation-in-part of application No. 08/639,132, filed on Apr. 26, 1996, now abandoned.

(51) Int. Cl.[7] ..................... A61K 31/195; A61K 31/215
(52) U.S. Cl. ..................... 514/561; 514/529; 514/530; 562/507; 562/553
(58) Field of Search ................. 514/529, 530, 514/561; 562/507, 553

(56) References Cited

U.S. PATENT DOCUMENTS

| | | | | |
|---|---|---|---|---|
| 4,087,544 A | * | 5/1978 | Satzinger et al. | 514/530 |
| 4,894,476 A | | 1/1990 | Butler et al. | 562/504 |
| 4,956,473 A | | 9/1990 | Mettler et al. | 548/408 |
| 4,958,044 A | | 9/1990 | Mettler et al. | 558/431 |
| 4,960,931 A | | 10/1990 | Butler et al. | 562/504 |
| 5,025,035 A | | 6/1991 | Wallace | 514/530 |
| 5,068,413 A | | 11/1991 | Steiner et al. | 562/507 |
| 5,084,479 A | | 1/1992 | Woodruff | 514/530 |
| 5,091,567 A | | 2/1992 | Geibel et al. | 562/507 |
| 5,095,148 A | | 3/1992 | Mettler et al. | 562/507 |
| 5,130,455 A | | 7/1992 | Mettler et al. | 558/426 |
| 5,132,451 A | | 7/1992 | Jennings et al. | 562/507 |
| 5,136,091 A | | 8/1992 | Mettler et al. | 562/507 |
| 5,149,870 A | | 9/1992 | Mettler et al. | 562/507 |
| 5,248,678 A | | 9/1993 | Costa et al. | 514/220 |
| 5,302,583 A | | 4/1994 | Costa et al. | 514/30 |
| 5,319,135 A | | 6/1994 | Jennings et al. | 62/507 |
| 5,332,736 A | | 7/1994 | Carmosin et al. | 514/235.5 |
| 5,362,860 A | | 11/1994 | Huang et al. | 536/4.1 |
| 5,362,883 A | | 11/1994 | Jennings et al. | 548/408 |
| 5,510,381 A | | 4/1996 | Pande | 514/561 |
| 5,563,175 A | * | 10/1996 | Silverman et al. | 514/561 |
| 5,792,796 A | * | 8/1998 | Woodruff et al. | 514/561 |

FOREIGN PATENT DOCUMENTS

| | | | |
|---|---|---|---|
| WO | 93/23383 | * | 11/1993 |
| WO | 96/03122 | | 2/1996 |

OTHER PUBLICATIONS

Yuen et al. "Enantioselective synthesis of . . . " Ca 121:49606, 1994.*
Bernasconi et al. "Biochemical aspects of . . . " CA 101:144002, 1984.*
Martin et al. "Bezodiazepine recognition site . . . ." CA 131:332173, 1999.*
Meyersburg et al. "A reverberating psychic mechanism . . . " EMABSE 75153516, 1974.*
Walden et al. "Value of old and new anticonvulsants . . . " MEDLINE 96058320, 1995.*
Zaccara et al. "Clinical pharmacokinetics . . . " TOXLINE 1989:58951, 1988.*
Roy–Byrne et al. "Valproated in anxiety . . . " TOXLINE 1989:52799, 1989.*
Ralph Ryback, M.D. and Lucas Ryback, "Gabapentin for Behavioral Dyscontrol", 'Letters to the Editor', *American Journal of Psychiatry*, vol. 152, No. 9, Sep. 1995, p. 1399.
Rock et al., "Gabapentin Actions on Ligand– and Voltage–Gated Responses in Cultured Rodent Neurons", CA 120:153636, 1993.
Watson et al., "Gabapentin Reduces Signs of Anxiety . . . ", Br. J. Pharm., vol. 116, p. 33P, 1995.

* cited by examiner

*Primary Examiner*—Ceila Chang
(74) *Attorney, Agent, or Firm*—Vidas,Arrett&Steinkraus PA.

(57) ABSTRACT

Treatment of the anxiety disorders and insomnia in humans may be accomplished by administering gabapentin in an effective amount.

3 Claims, No Drawings

METHOD FOR TREATING ANXIETY, ANXIETY DISORDERS AND INSOMNIA

CROSS-REFERENCE TO RELATED APPLICATIONS

This application is a Continuation-In-Part from application Ser. No. 08/639,132 filed Apr. 26, 1996, now abandoned.

BACKGROUND OF THE INVENTION

1. Field of the Invention

This invention relates to treatment of anxiety, including all of the anxiety disorders, and insomnia in humans by administration of gabapentin, its derivatives and pharmaceutically acceptable salts.

2. Description of the Related Art

Gabapentin is a generic term used to identify the chemical compound (1-aminomethyl)-1-cyclohexaneacetic acid. It is useful in therapy of certain cerebral disorders such as certain forms of epilepsy, faintness attacks, hypokinesia and cranial traumas. U.S. Pat. Nos. 4,024,175 and 4,087,544 cover the compound and its uses. They also disclose an acid salt, i.e. gabapentin hydrochloride hydrate in a ratio of 4:4:1 and a sodium salt of gabapentin hydrate in a ratio of 2:1. These patents are hereby incorporated by reference. Pregabalin is a long-acting form of gabapentin with the formula (S)-3-(aminomethyl)-5-methyl-hexanoic acid and CAS Registry Number: 148553-50-8, CI 1008. The compounds are described in U.S. Pat. Nos. 5,608,090 and 5,599,973, the disclosure of which are incorporated herein by reference to show additional forms of gabapentin usable in this invention.

U.S. Pat. No. 5,084,479 states that compounds such as gabapentin are used for treating neurodegenerative disorders, perinatal asphyxia, status epilepticus, Alzheimer's, Huntington's, Parkinson's, and Amyotrophic Lateral Sclerosis. That invention covers treating neurodegenerative disorders termed acute brain injury. These include but are not limited to: stroke, head trauma, and asphyxia.

U.S. Pat. No. 5,189,026 describes the use of ivermectin, and notes that other GABA agonists may have activity to some extent in treating anxiety, but dismisses them due to stated detrimental effects.

WO 9603122 is a published application entitled "Controlling Anxiety and Panic —By Administration of Aminomethyl-cycloalkane Acetate(s), Esp. Gabapentin", filed by BROWN, J. P.; GEE, N. S.; SINGH, L.; WOODRUFF, G. N.; and BROWN, J. That application claims a priority to U.S. application Ser. Nos. 08/281,285, filed Jul. 27, 1994, and 08/445,398, filed Jun. 6, 1995.

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. § 1.56(a) exists.

SUMMARY OF THE INVENTION

It has been found that gabapentin surprisingly has properties that also enables it to be used effectively to treat anxiety and all of the anxiety disorders, and may also be used to treat patients with insomnia. The etiology of anxiety and the anxiety disorders is unknown and the biochemical defect is also unknown. We postulate that the specific effect of gabapentin on insomnia, anxiety and the anxiety disorders implicates an indirect involvement with gamma aminobutyric acid (GABA) in its mechanism of action, as is the case for another group of drugs, the benzodiazepines, with their effects on anxiety and insomnia. It has been found that benzodiazepines act through their own benzodiazepine receptor which is coupled with the GABA receptor. We suggest that gabapentin does the same through its own receptor, which we name the Gabapentin receptor, also coupled with the GABA receptor. We propose that the gabapentin receptor is coupled with one of the subunits ($\alpha$, $\beta$, $\delta$ or $\epsilon$) of the $GABA_A$-receptor. This surprising finding has never been suggested or proposed previously. The clinical effects observed have lead us to this conclusion. Use of the term "gabapentin" in this application is intended to encompass gabapentin, pregabalin and their pharmaceutically acceptable salts.

DESCRIPTION OF THE PREFERRED EMBODIMENTS

The anxiety disorders are described succinctly in the *American Psychiatric Association Diagnostic and Statistical Manual*, 4th edition, DSM IV, the disclosure of which is incorporated herein by reference. The anxiety disorders have been divided into three major clinical entities: generalized anxiety, panic disorder with or without agoraphobia, and obsessive-compulsive disorders (DSM-III-R).

Generalized anxiety disorder (GAD) is characterized by intense fearfulness expressed through symptoms that can affect almost all anatomic body regions. In cases of panic attacks associated or not with panic disorder, anxiety symptoms are associated with recognizable panic attacks, with or without agoraphobia. The essential feature of a Panic Attack is a discrete period of intense fear or discomfort that is accompanied by at least 4 to 13 somatic or cognitive symptoms,. Panic Attacks can occur in a variety of Anxiety Disorders (e.g., Panic Disorders, Social Phobia, Posttraumatic Stress Disorder). Essential and specific features of GAD remain to be the presence of unrealistic and inappropriate apprehensive expectation, which may persist for several months and be associated to secondary symptoms, including signs of vigilance (irritability, insomnia, difficulty concentrating), motor tension (trembling, muscle tension, restlessness, fatigability), and autonomic hyperactivity (cardiac palpitations, shortness of breath, smothering sensations, sweatiness of hands and skin).

Anxiety can also be part of other psychiatric disorders and considered secondary to a primary psychopathology, such as major depression, mania or schizophrenia. Antianxiety or hypnotic drugs are given primarily for the treatment of minor or major generalized anxiety disorder, with or without insomnia as a target symptom (primary), but also where it coexists with another psychiatric disorder (secondary). The most common drugs used to treat anxiety disorders have been the benzodiazepines.

The sleep disorders are organized into four major sections according to presumed etiology. The sleep disorders are also succinctly described in the *American Psychiatric Association Diagnostic and Statistical Manual*, 4th edition, DSM IV and generally include primary sleep disorders, sleep disorders related to another mental disorder, sleep disorder due to a general medical condition and substance-induced sleep disorder. In this application, insomnia shall be used as a short-hand for all of the sleep disorders.

Based on our research, it is apparent that gabapentin may be used to safely treat all of these illnesses, and also to treat minor or transient anxiety symptoms that do not fulfill diagnostic criteria for which a patient may seek medications from a physician, without fear of long term physical addiction or other benzodiazepine side effects.

Case History 1

Mr. S. is a 64 year-old retired patient. His family history reveals that his sister has manic depressive illness and maternal aunts are described as "nervous". In his medical history, there is a cervical laminectomy (1988). He reports residual pain and weakness in the right arm and right leg and chronic neck pain. He has a history of three months of depression with no treatment (1989) and a history of chronic severe generalized anxiety disorder.

In December 1994, the patient had been taking a benzodiazepine, clonazepam 2.5 mg/day, for the last five years when his anxiety and depression became much worse. Anxiety was associated with marked insomnia and significant situational stressors (financial and marital). Fluoxetine and then sertraline was initiated at a low dose, but made the patient worse. Gabapentin was initiated 300 mg/day (October 1994) and slowly increased. The response was immediate; sleep improved and anxiety decreased. Patient is now functional for the first time in many years. Improvement continues as of this day. His psychological dependency on benzodiazepines has significantly decreased since the intake of gabapentin. Improvement persists. With gabapentin we have noticed an improvement in mood and a marked improvement in sleep and anxiety, in addition to an analgesic effect.

Case History 2

Mrs. R. is a 62 year-old retired patient with a family history of bipolar affective illness. The patient has been treated for manic-depressive illness since she experienced her first depressive episode at the age of 42 (1975) and was hospitalized several times for mania and depression.

At the age of 46 (1979), the patient was hospitalized for an episode of acute mania. After that, she was treated with lithium, tryptophan, nicotinamide, clonazepam, Premarin®, Provera® and Overal®. The patient was re-hospitalized for a manic episode at the age of 50 (1982). She has been treated with various psychotropic drugs, especially: lithium, tryptophan, and clonazepam. Lithium was discontinued in October 1983 until 1985. She was given tryptophan, lecithin and female hormones for control of a severe rapid-cycling bipolar disorder. Fluoxetine, as well as, antiepileptics (carbamazepine and valproic acid) were also added to her treatment.

Due to the patient's fast cycling manic depressive illness, her medication is regularly adjusted. Since 1991 magnesium was added to her regular medication. In June 1992, carbamazepine was changed to valproic acid but discontinued in December 1992 because the patient was losing hair. In April 1993, risperidone was initiated and in March 1994 lithium was discontinued. She is currently treated with risperidone, gabapentin 1800 mg QD (initiated in August 1994), clonazepam and ritanserin was recently added to her treatment in an attempt to improve her mood. She also takes magnesium and lecithin. The beneficial effects of gabapentin were on anxiety associated with depression and sleep. Every time gabapentin is decreased, severe anxiety symptoms return.

Case History 3

Mrs. D. is a 47 year-old single woman who is working as a freelance writer. Her family history reveals mainly manic-depressive illness in her father's line. She was hospitalized at the age of 25 (1972) because of severe depression and a suicide attempt by drug overdose. The patient has taken lithium since 1973. She has also had panic attacks since 1978.

In January 1994, the patient was depressed and valproic acid was initiated with lithium and clonazepam. Two weeks later, the patient improved. In October 1994, valproic acid was discontinued because she was losing her hair. Gabapentin 300 mg BID up to 300 mg TID was initiated in her treatment. Gabapentin was decreased to 100 mg HS because the patient complained of sedation. Discontinuation of gabapentin results in a return of panic attacks and anxiety disorder. The patient has remained on gabapentin with a persistent beneficial effect on panic attacks and anxiety.

Case History 4

Mrs. M. is a 21 year-old single woman who lives with her mother. She has a family history of schizophrenia and depression. Patient's medical history revealed that at an age of three she had a brain trauma. She was treated for agoraphobia at age 12 and has had episodes of anorexia. Before her first hospitalization in 1992, the patient had not been outside of her home for one year and she was totally inactive at home. The patient was first admitted, at the age of 19, for two months for her first episode of paranoid schizophrenia. Neuroleptic treatment was initiated.

In September 1993, the patient was referred for follow up. Her antipsychotic medication was gradually decreased to initiate risperidone. In January 1994, the patient had improved, but still had drug-induced akathisia and tardive dyskinesia. Valproic acid was initiated because of therapeutic drug resistance (May 1994).

In February 1995, gabapentin was started at 100 mg QD and increased to 600 mg QD, valproic acid was decreased to 750 mg QHS with risperidone 4 mg AM and 3.5 mg HS and procyclidine 15 mg BID. The main effect of gabapentin has been to potentiate neuroleptics, decrease the level of anxiety and panic attacks, and improve sleep. The patient no longer has agoraphobia. She has been able to form a relationship (boyfriend) outside of her immediate family.

Case History 5

Mr. S. is a 21 year-old single man of Arabic origin who is still studying at University. His medical history is unremarkable. The patient was first seen by a psychiatrist at the age of 18 and followed for obsessive compulsive disorder (OCD) in the United Emirates; the patient tended toward isolativeness. Also, he developed a tic disorder and complained of anxiety.

In February 1994, the patient developed intense paranoid ideation and became more withdrawn. Over the previous two years, the patient had suffered from paranoid delusions and auditory hallucinations. He stopped taking his neuroleptic medication in mid-December while he was a University student. He was admitted as an inpatient in March 1994. The patient was tried on risperidone but did not improve. He was started on clozapine and the psychotic symptoms improved considerably with reduced auditory hallucinations and delusional thinking. The patient was discharged with clozapine and lorazepam. In June, the patient was referred for Follow-Up where an anticonvulsant drug, valproic acid was added to potentiate clozapine, but discontinued in August 1994.

In January 1995, procyclidine 5 mg BID was initiated because the patient experienced akathisia; he improved with this medication. In February 1995, gabapentin was added to the patient's treatment. The patient reported dizziness during the increase of gabapentin but this subsided. Currently, the patient takes clozpine 125 mg BID, fluoxetine mg QD, gabapentin 500 mg HS and procyclidine 5 mg BID. The main beneficial effect of gabapentin, as opposed to valproic acid, has been on obsession, anxiety and sleep. We noticed a marked reduction in the level of anxiety (generalized anxiety) and OCD with gabapentin.

Dosages

The usual dosage levels will vary depending upon the patient. However, treatment of the various anxiety disorders will usually entail administering from between about 100 mg/day to about 1800 mg/day of gabapentin, which may be given in any vehicle under which that drug is formulated, including orally. The preferred range may be between about 300 mg/day to 1800 mg/day. The therapeutic benefit of controlling insomnia (primary and secondary) that was seen indicates that a dosage of from about 100 mg to about 400 mg/day at bedtime may provide good results to such patients. The drug appears ideal for the elderly with anxiety and/or insomnia. The dosage for panic disorders may require dosages in the range of between about 3000 to 3600 mg/day of gabapentin.

In this application, "panic attacks" are considered to be covered by the term "anxiety" or "anxiety disorder". Use of those terms in the claims also refers to "panic attacks." While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

This completes the description of the preferred and alternate embodiments of the invention. Those skilled in the art may recognize other equivalents to the specific embodiment described herein which equivalents are intended to be encompassed by the claims attached hereto.

What is claimed is:

1. A method for preventing, treating or controlling primary insomnia in humans which comprises administering to a patient in need of such preventing, treating or controlling an effective amount of gabapentin or a pharmaceutically acceptable salt thereof.

2. The method of claim 1 wherein said gabapentin is administered at between about 100 to about 400 mg per day.

3. A method for preventing, treating or controlling primary insomnia in humans which comprises administering to a patient in need of such preventing, treating or controlling an effective amount of pregabalin or a pharmaceutically acceptable salt thereof.

* * * * *